United States Patent [19]

Shealy et al.

[11] Patent Number: 4,719,214

[45] Date of Patent: Jan. 12, 1988

[54] CARBOCYCLIC ANALOGUES OF THYMINE NUCLEOSIDES

[75] Inventors: Y. Fulmer Shealy; C. Allen O'Dell, both of Birmingham, Ala.

[73] Assignee: Southern Research Institute, Birmingham, Ala.

[21] Appl. No.: 758,719

[22] Filed: Jul. 25, 1985

[51] Int. Cl.[4] .................. A61K 31/505; C07D 239/26
[52] U.S. Cl. ..................................... 514/274; 544/229; 544/314
[58] Field of Search ................. 544/314, 229; 514/274

[56] References Cited

U.S. PATENT DOCUMENTS 4,396,623  8/1983  Shealy et al. .................. 544/309
4,415,573 11/1983  Ochi et al. ..................... 544/314
4,564,618  1/1986  Scopes et al. ................... 514/274

FOREIGN PATENT DOCUMENTS 2084152  4/1982  United Kingdom ............... 544/314

OTHER PUBLICATIONS

Shealy and Clayton, Journal of the American Chemical Society, vol. 88, pp. 3885-3887, 1966.
C. Desgranges et al., (Biochemical Pharmacology, vol. 32, pp. 3583-3590, 1983).
R. Kaul, K. Keppeler, G. Kiefer, B. Hempel, and P. Fischer, (Chemosphere, vol. 11, pp. 539-540, 1982).
Y. F. Shealy and C. A. O'Dell, Journal of Heterocyclic Chemistry, vol. 13, pp. 1041-1047 (1976).
Shealy, O'Dell and Thorpe, Journal of Heterocyclic Chemistry, vol. 18, pp. 383-389 (1981).
Shealy, O'Dell, Thorpe and Coburn, Jr. Journal of Heterocyclic Chemistry, vol. 20, pp. 655-661 (1983).
K. C. Murdock and R. B. Angier, Journal of the American Chemical Society, vol. 84, pp. 3758-3764.
Shealy et al., Journal of Medicinal Chemistry, vol. 26, pp. 156-161 (1983).
Jerry March, "Advanced Organic Chemistry," 2nd Ed., McGraw-Hill Book Co., 1977, New York, N.Y.
Jasenka Matulic-Adamic and Kyoichi A. Watanabe, J. Chem. Soc., Chem. Comm., 1985, pp. 1535-1536.
Shealy et al., Chemical Abstract, vol. 104 (1986): 69111v.
Maggiora et al., Chemical Abstracts, vol. 104, (1986): 130206y.
Shealy et al., Chemical Abstracts, vol. 104, (1986): 130207z.

Primary Examiner—Donald G. Daus
Assistant Examiner—Barbara Cassatt
Attorney, Agent, or Firm—Roylance, Abrams, Berdo & Goodman

[57] ABSTRACT

There are disclosed compounds having the formula:

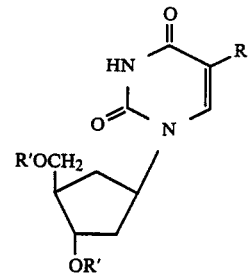

wherein R is a group having the formula —C≡C-Si(CH$_3$)$_3$, —C≡CH, —CH=CH$_2$, —CH$_2$CH$_2$Si(CH$_3$)$_3$ or —CH$_2$X; X is bromo, chloro or iodo; and R' is hydrogen or an acyl group, with the proviso that when R is —CH$_2$X, R' is an acyl group. Certain of these compounds are active in inhibiting the replication of DNA viruses. Other of these compounds are useful as intermediates in the production of compounds which are active in inhibiting the replication of DNA viruses.

15 Claims, No Drawings

CARBOCYCLIC ANALOGUES OF THYMINE NUCLEOSIDES

BACKGROUND OF THE INVENTION

This invention relates to the preparation of carbocyclic analogues of thymine nucleosides, to the use of such compounds in the treatment of viral infections, and to certain novel compounds.

Thymidine is 5-methyl-2'-deoxyuridine. Therefore, carbocyclic analogues of thymine nucleosides are also carbocyclic analogues of 5-substituted-2'-deoxyuridines.

The term "carbocyclic analogue of a nucleoside" designates a compound that has the same chemical structure as the nucleoside except that the oxygen atom of the furanose moiety of the nucleoside is replaced by a methylene group in the carbocyclic analogue; or, differently expressed, in the carbocyclic analogue a cyclopentane ring replaces the tetrahydrofuran ring of the analogous nucleoside. Such nucleoside analogues were designated carbocyclic analogues of nucleosides by Shealy and Clayton, *Journal of the American Chemical Society,* Volume 88, pages 3885–3887, 1966. The natural nucleosides and many of their true nucleoside analogues are subject to the action of enzymes (phosphorylases and hydrolases) that cleave the nucleosides to the pentose and purine or pyrimidine moieties. For example, it has been reported by C. Desgranges et al. (*Biochemical Pharmacology,* Vol. 32, pages 3583–3590, 1983) that various 5-substituted-2'-deoxyuridines including 5-ethyl-2'-deoxyuridine (EDU) and 5-[(E)-2-(bromovinyl)]-2'-deoxyuridine (BVDU) are substrates for thymidine phosphorylase isolated from human blood platelets. Furthermore, R. Kaul, K. Keppeler, G. Kiefer, and B. Hempel (*Chemosphere,* Vol. 11, pages 539–540, 1982) reported the identification of the cleavage products 5-ethyluracil and 5-(2-hydroxyethyl)uracil as metabolites of EDU in rats. The biological effects of such true nucleoside analogues may be lessened by the action of these degradative enzymes. In contrast, carbocyclic analogues of nucleosides do not possess the glycosidic bond present in the true nucleosides and, therefore, are not subject to the action of these degradative enzymes. They may also be more selective in their biological actions.

The synthesis of the carbocyclic analogue (Formula I, R=CH$_3$) of thymidine was first reported by Y. F. Shealy and C. A. O'Dell in the *Journal of Heterocyclic Chemistry,* Volume 13, pages 1041–1047 (1976). Additional properties of the carbocyclic analogue of thymidine and the synthesis and properties of two related carbocyclic analogues of thymine nucleosides were reported by Shealy, O'Dell, and Thorpe in the *Journal of Heterocyclic Chemistry,* Volume 18, pages 383–389 (1981). In this latter article in the *Journal of Heterocyclic Chemistry* and in an article by Shealy, O'Dell, Thorpe and Coburn, Jr., in the *Journal of Heterocyclic Chemistry,* Volume 20, pages 655–661 (1983), it was shown that a claim [K. C. Murdock and R. B. Angier, *Journal of the American Chemical Society,* Volume 84, pages 3758–3764 (1962)] that the carbocyclic analogue of thymidine had been synthesized earlier was erroneous.

Antiviral activity by the carbocyclic analogue of thymidine and by other 5-substituted-2'-deoxyribofuranosides was disclosed by Shealy et al. in an article in the *Journal of Medicinal Chemistry,* Volume 26, pages 156–161 (1983). U.S. Pat. No. 4,396,623 to Shealy et al discloses a method for the treatment of viral infections by treating a host animal with a pharmaceutically effective amount of a carbocyclic analogue of a nucleoside represented by the formula:

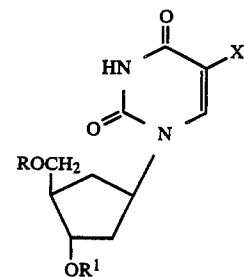

wherein X is chlorine, bromine, iodine, a lower alkyl group or an amino group of the formula —NHR$^2$ wherein R$^2$ is a lower alkyl group; and R and R$^1$ can be the same or different members selected from the group consisting of hydrogen, an alkanoyl group or an aroyl group.

SUMMARY OF THE INVENTION

In accordance with this invention, there are provided compounds having the formula:

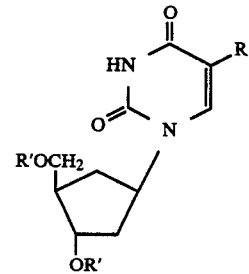

wherein R is a group having the formula —C≡C-Si(CH$_3$)$_3$, —C≡CH, —CH=CH$_2$, —CH$_2$CH$_2$Si(CH$_3$)$_3$ or —CH$_2$X; X is a bromo, chloro or iodo; and R' is hydrogen or an acyl group, preferably one having from 2–7 carbon atoms, with the proviso that when R is —CH$_2$X, R' is an acyl group. Certain of these compounds are active in inhibiting the replication of DNA viruses. Other of these compounds are useful as intermediates in the production of compounds which are active in inhibiting the replication of DNA viruses.

DETAILED DESCRIPTION OF THE INVENTION

Carbocyclic analogues of 5-substituted-2'-deoxyuridines represented by Formula I

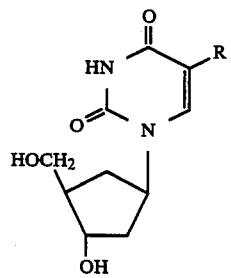

Formula I may be obtained by synthesis routes that begin with the carbocyclic analogue of 2'-deoxyuridine, which is represented by Formula 1. (All Arabic formula numbers refer to the formulas shown in the Charts A and B.) Examples of such routes are outlined in Chart A. In these routes, a 5-halo-2'-deoxyuridine analogue (Formula 4) is prepared as described by Shealy et al. in U.S. Pat. No. 4,396,623 and in the *Journal of Medicinal Chemistry*, Volume 26, pages 156–161 (1983) or as described in Example 2 herein. From 5-halo-2'-deoxyuridine analogues, 5-ethynyl derivatives, such as the 5-(trimethylsilylethynyl) derivative (Formula 5), may be prepared. Conversion of the 5-(trimethylsilylethynyl) derivative to the carbocyclic analogue (Formula 6, R=H) of 5-ethynyl-2'-deoxyuridine may be effected in basic media. The carbocyclic analogue (C-EDU; Formula 8 with R=H) of 5-ethyl-2'-deoxyuridine is obtained by reduction of the 5-ethynyl derivative (Formula 6, R=H) by catalytic hydrogenation. Furthermore, the trimethylsilyl derivatives of C-EDU (Formula 7 with R=H or acetyl) are obtained following catalytic hydrogenation of the trimethylsilylethynyl derivative (Formula 5 with R=acetyl). Partial reduction of the 5-ethynyl derivative (Formula 6) by hydrogenation over a less active catalyst, such as the Lindlar catalyst, produces the 5-ethenyl derivative (Formula I, R=—CH=CH$_2$) which can be further reduced to C-EDU.

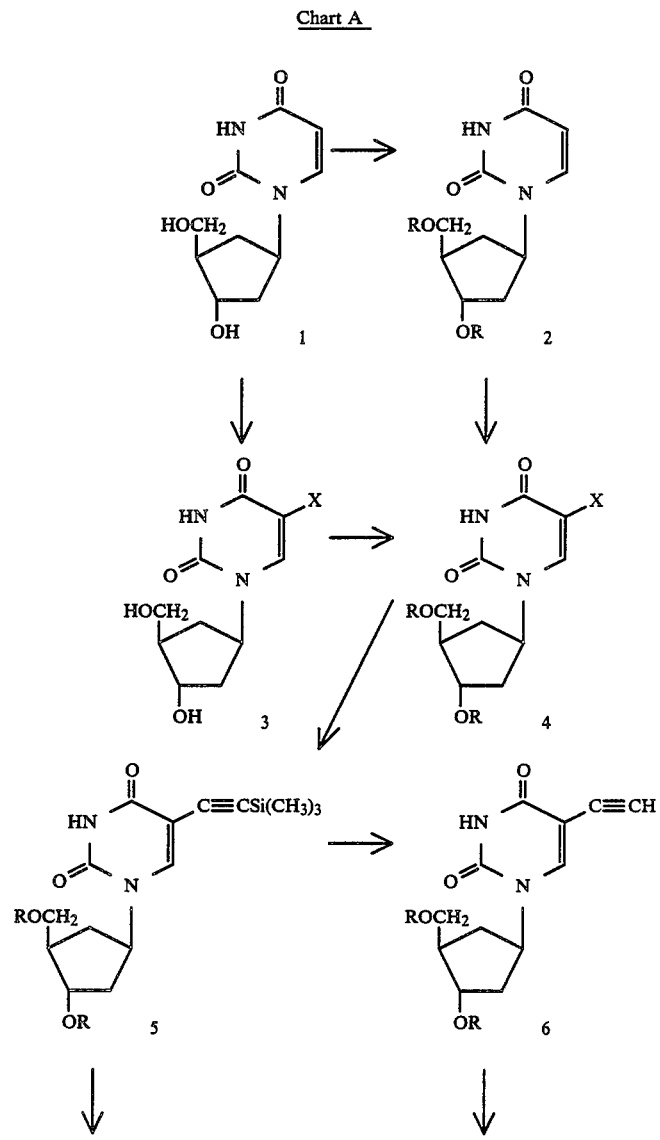

Chart A

Chart A

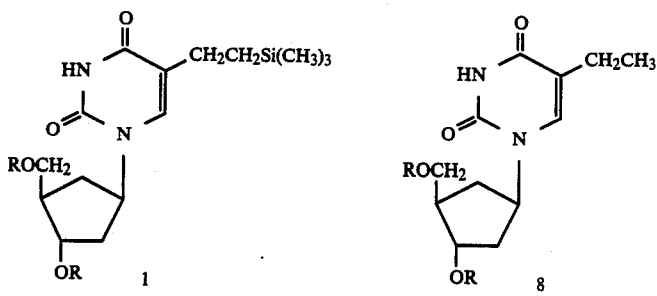

Chart B

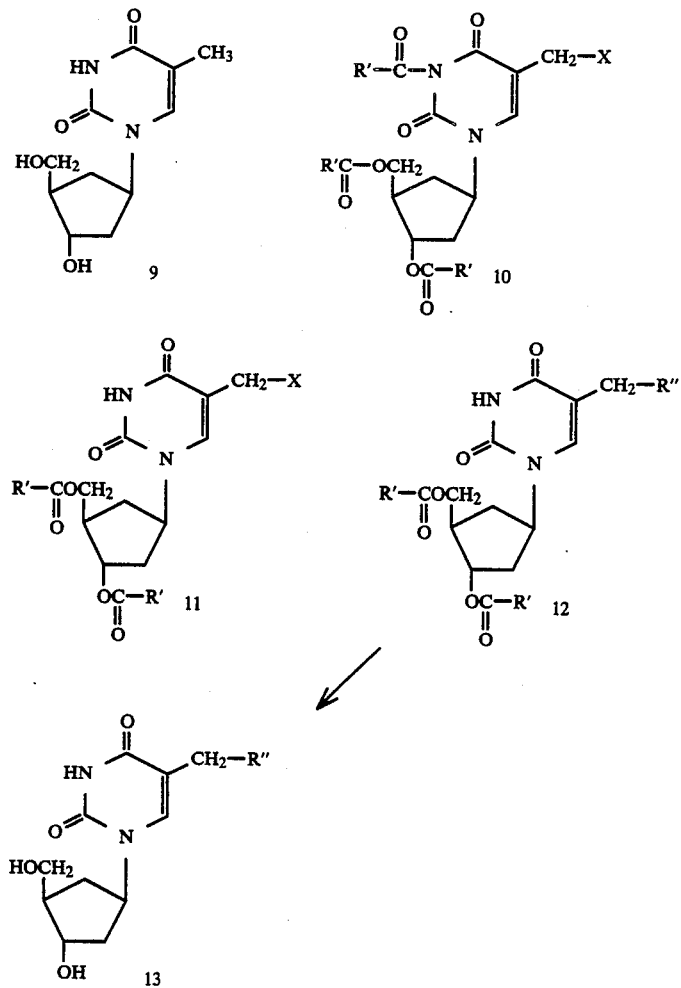

Carbocyclic analogues of 5-substituted 2'-deoxyuridines represented by Formula I may be obtained also by synthesis routes that begin with the carbocyclic analogue of thymidine, which is represented in Chart B by Formula 9. In these routes, a replaceable substituent is introduced into the methyl group of the carbocyclic analogue (Formula 9) of thymidine or a deriviative thereof (for example, Formulas 10 and 11 with X=H). Such a replaceable group may be a halogen such as chlorine, bromine, or iodine. The replaceable group is then replaced by an alkyl, an alkenyl, an alkynyl, or an aralkyl group. Replacement of the replaceable group may be effected by means of an alkyl, alkenyl, alkynyl, or aralkyl organometallic reagent.

The synthesis routes of Chart B are illustrated as follows. A tribenzoyl derivative of the carbocyclic analogue (Formula 9) of thymidine is prepared by treating this carbocyclic analogue with benzoyl chloride in pyridine. The tribenzoyl derivative, which is represented by Formula 10 wherein X=H and R'=phenyl, is then converted in weakly acidic media to a dibenzoyl derivative (Formula 11 with X=H and R'=phenyl) of the carbocyclic analogue of thymidine. The introduction of a bromo substituent on the methyl group of the dibenzoyl derivative, or of a similar diacyl derivative such as the analogous diacetyl derivative, produces the desired 5-(bromomethyl)-2'-deoxyuridine analogue (Formula 11 with X=Br). The obtention of a diacyl 5-substituted-2'-deoxyuridine analogue represented by Formula 12 is effected by treating the 5-(bromomethyl) derivative (Formula 11) with an organometallic reagent such as lithium dimethylcopper, i.e. $(CH_3)_2CuLi$. Diacyl derivatives represented by Formula 12 are converted to the carbocyclic analogue (Formula 13), such as C-EDU, by standard procedures, such as the use of basic media. Alternatively, the tribenzoyl 5-(bromomethyl) derivative represented by Formula 10 with X=Br may be treated with an organometallic reagent to introduce the desired alkyl, alkenyl, alkynyl, or aralkyl substituent; the benzoyl groups may then be removed in basic media in order to obtain the desired 5-substituted 2'-deoxyuridine analogue represented by Formula 13.

As shown in Table 1, Example 14, the selective antiviral activities (VR) of C-EDU versus type 1 herpes simplex virus (HSV-1) and type 2 herpes simplex virus (HSV-2) are comparable to those of 9-β-D-arabinofuranosyladenine (Ara-A), a prescription antiviral drug. Furthermore, C-EDU is as active vs. HSV-1 as is the corresponding true nucleoside, 5-ethyl-2'-deoxyuridine (EDU), which is also a clinically active drug. C-EDU also has definite and significant activity against HSV-2. However, unlike EDU, which possesses a glycosidic bond that can undergo enzymatic scission to 5-ethyluracil or a derivative thereof (e.g., as reported by Kaul, Keppeler, Kiefer, and Hempel, loc. cit.), C-EDU is not subject to the degradative actions of phosphorylases and hydrolases because it is a 1-cycloalkyl-2,4(1H,3H)-pyrimidinedione. The carbocyclic analogue (Formula 6 with R=H, Example 4) of 5-ethynyl-2'-deoxyuridine also has significant antiviral activity vs. both HSV-1 and HSV-2. The carbocyclic analogue (Formula 7 with R=H, Example 7) of 5-trimethylsilylethyl-2'-deoxyuridine also has antiviral activity vs. HSV-1.

Compounds prepared in accordance with this invention are illustrated by, but are not limited to, the following examples. The system of designating the orientation of substituents on the cyclopentane ring as α or β is that used by *Chemical Abstracts,* beginning with Volume 76, in the *Chemical Substance Index.* In the examples illustrating syntheses of the compounds of this invention, data were acquired and are reported as follows. Decomposition and melting temperatures (mp) were determined in capillary tubes. Ultraviolet spectra (UV) were recorded with a recording spectrophotometer and absorption maxima are reported in nanometers; sh=shoulder. Solutions for ultraviolet spectral determinations were prepared by diluting a 5-mL aliquot of a water or ethanol solution to 50 mL with 0.1N hydrochloric acid, phosphate buffer (pH 7), or 0.1N sodium hydroxide. Absorption maxima of these solutions are reported as being determined at pH 1, 7, or 13, respectively. Infrared spectra (IR) were recorded from samples in pressed potassium bromide discs; s=strong, vs=very strong, sh=shoulder, w=weak. Mass spectral data (MS) were taken from low-resolution, electron-impact spectra determined at 70 eV or from spectra determined by the fast-atom-bombardment (FAB) method. The peaks listed are those arising from the molecular ion (M), those attributable to the loss of certain fragments (M minus a fragment), and some other prominent peaks. Fragments containing the complete pyrimidine moiety may be designated P plus an atom or group. Nuclear magnetic resonance spectra were determined at 300.64 MHz for proton ($^1$H NMR) spectra. The internal standard was tetramethylsilane; s=singlet, t=triplet, q=quartet, qn=quintet, m=multiplet. Thin-layer chromatography (TLC) was performed on plates of silica gel, the developing solvent is specified parenthetically, and developed plates were examined by ultraviolet light.

EXAMPLE 1

1-[(1α,3β,4α)-3-Hydroxy-4-(hydroxymethyl)cyclopentyl]-2,4-(1H,3H)-pyrimidinedione Diacetate (Formula 2, R=CH$_3$CO—)

A solution (protected from atmospheric moisture) of 0.63 mL of acetic anhydride, 10 mL of anhydrous pyridine, and 0.5 g of the carbocyclic analogue (Formula 1) of 2'-deoxyuridine was stirred at room temperature for 21 hr. The reaction solution was then concentrated under reduced pressure by means of a vacuum (oil) pump. The residue was mixed well with water (2 mL), the mixture was concentrated in vacuo, the solid residue was triturated with ethyl acetate (5 mL), and this mixture was placed in a refrigerator. The white crystalline solid was separated by filtration, washed with ethyl acetate, and dried in vacuo at 56° C.: yield, 476 mg (70%); mp 110°–112° C.; TLC, 1 spot (9:1 chloroform-methanol); MS (electron-impact, direct-probe temperature 20° C.), m/e 310 (M), 250 (M—CH$_3$COOH), 207, 189, 177, 147, 139 (P+C$_2$H$_4$), 134, 113, (P+2H), 112 (P+H), 96.

Analysis. Calcd. for C$_{14}$H$_{18}$N$_2$O$_6$: C, 54.19; H, 5.85; N, 9.03. Found: C, 53.85; H, 5.69; N, 8.89.

EXAMPLE 2

1-[(1α,3β,4α)-3-Hydroxy-4-(hydroxymethyl)cyclopentyl]-5-iodo-2,4(1H,3H)-pyrimidinedione Diacetate (Formula 4, X=I, R=CH$_3$CO—)

Method A. As revealed in U.S. Pat. No. 4,396,623, Aug. 2, 1983, the carbocyclic analogue of 5-iodo-2'-deoxyuridine (Formula 3, X=I) was prepared by treating the carbocyclic analogue (Formula 1) of 2'-deoxyuridine with iodine and nitric acid. The compound represented by Formula 4 with X=I and R=acetyl was prepared, as revealed in the aforementioned U.S. Pat. No. 4,396,623, by treating the carbocyclic analogue of 5-iodo-2'-deoxyuridine with acetic anhydride in pyridine.

Method B. The compound of this Example was also prepared by a new method comprised of the treatment of the compound of Example 1 with iodine monochloride. This method is illustrated by the following procedure.

A solution (protected from atmospheric moisture) of dichloromethane (17 mL), iodine monochloride (0.1 mL), and the compound (460 mg.) of Example 1 (Formula 2, R=acetyl) was boiled under reflux for 3 hr. The reaction solution was cooled to room temperature and diluted with water (14 mL), and an aqueous solution of sodium hydrogen sulfite (2%) was added dropwise to the vigorously stirred solution until its purple color disappeared. Dichloromethane was evaporated under reduced pressure from the solution, and the resulting mixture, containing a white precipitate, was placed in a refrigerator overnight. The white solid precipitate was collected by filtration, washed well with cold water, and dried in vacuo at 56° C.: yield, 580 mg. (89.6%); mp 176°–178° C. This material was recrystallized from methanol: weight of recrystallized product, 530 mg (91% recovery); mp 180°–184° C.

EXAMPLE 3

1-[(1α,3β,4α)-3-Hydroxy-4-(hydroxymethyl)cyclopentyl]-5-(trimethylsilylethynyl)-2,4(1H,3H)-pyrimidinedione Diacetate (Formula 5, R=CH$_3$CO—)

A suspension of 750 mg of the carbocyclic analogue (Formula 4 with X=I and R=acetyl) of 5-iodo-2'-deoxyuridine diacetate in triethylamine (75 mL) was vigorously deoxygenated by bubbling argon through the mixture. To this mixture, under an atmosphere of argon, was added (trimethylsilyl)acetylene (0.75 mL), bis(triphenylphosphine)palladium(II) chloride (25 mg), and cuprous iodide (25 mg), and the resulting mixture was stirred under argon at 50° C. for 3 hr. The reaction mixture was concentrated to dryness in vacuo; the dark, solid residue was dissolved in chloroform (100 mL), and the chloroform solution was washed twice with 50-mL portions of a 10% aqueous solution of the disodium salt of ethylenediaminetetraacetic acid and twice with 50-mL portions of water. The resulting chloroform solution was dried with magnesium sulfate, filtered, and concentrated in vacuo to a solid residue. The desired product was isolated by chromatography of the crude product on a column of silica gel 60 (50 g) with 9:1 chloroform-methanol as developing and eluting solvent. Fractions that were shown by TLC to contain the desired product were combined and concentrated in vacuo to a pale buff-colored solid; weight, 640 mg (91.8%) yield. A hot solution of this material in ethyl acetate was diluted with cyclohexane (12 mL), and the resulting solution was allowed to cool to room temperature and then placed in a refrigerator overnight. A white crystalline precipitate was collected by filtration, washed with cold cyclohexane, and dried in vacuo; yield, 525 mg (75%); mp 181°–184° C., UV max 298 nm ($\epsilon$ 14600) and 237 ($\epsilon$ 12200) at pH 1, 297 nm ($\epsilon$ 14800) and 236 ($\epsilon$ 12400) at pH 7, 288 nm ($\epsilon$ 9900) and 232 ($\epsilon$ 12200) at pH 13; MS (electron-impact, direct-probe temperature 20° C.), m/e 406 (M), 391 (M—CH$_3$), 346 (M—CH$_3$COOH), 331, 309, 289, 273, 271, 235 (P+C$_2$H$_4$), 208 (P+H), 199 (M—P), 193; IR (2200–1200 cm$^{-1}$ region) 2155 (—C≡C—), 1740 vs, 1725 s, 1680 vs, 1610, 1470, 1460 w, 1450 w, 1435, 1405, 1380, 1365, 1350 sh, 1340 sh, 1315, 1305, 1290, 1265 vs, 1255 sh, 1240, 1230; medium-strong IR bands at 1040, 890 and 845 cm$^{-1}$.

Analysis. Calcd. for C$_{19}$H$_{26}$N$_2$O$_6$Si: C, 56.13; H, 6.45; N, 6.89. Found: C, 56.06; H, 6.78; N, 6.95.

EXAMPLE 4

1-[(1α,3β,4α)-3-Hydroxy-4-(hydroxymethyl)cyclopentyl]-5-ethynyl-2,4(1H,3H)-pyrimidinedione (Formula 6, R=H)

A solution of 375 mg of the (trimethylsilyl)ethynyl derivative of Example 3 in 15 mL of a 0.2M solution of sodium methoxide in methanol was stirred under an argon atmosphere overnight at room temperature. The solution was diluted with water, and the proton form of a cation-exchange resin (previously washed with methanol) was added to the stirred mixture until the solution was approximately neutral (about pH 6). The resin was removed by filtration, the filtrate (combined with copious methanol washings of the residue) was treated with activated charcoal, and the resulting filtrate (plus methanol washings) was concentrated in vacuo. The amorphous residue was triturated with 9:1 chloroform-methanol, the solvents were evaporated in vacuo, the solid residue was dissolved in a mixture of ethanol (3 mL) and ether (10 mL), the mixture (containing a small amount of a curdy precipitate) was refrigerated and then filtered, and the filtrate was concentrated in vacuo to a gummy residue. The residue was triturated with ethyl acetate (4 mL) to induce crystallization, and the crystalline solid was collected by filtration, washed with ethyl acetate, and dried in vacuo at 56° C.: yield, 140 mg (61%); mp 190°–193° C.; MS (electron impact, direct-probe temperature 20° C.), m/e 250 (M), 206, 169, 163 (P+C$_2$H$_4$), 155, 137, (P+2H), 135 (P+H); UV max 292 nm ($\epsilon$ 11900) and 230 ($\epsilon$ 10100) at pH 1, 292 nm ($\epsilon$ 12000) and 230 ($\epsilon$ 10200) at zH 7, 288 nm ($\epsilon$ 9600) and 231 ($\epsilon$ 11300) at pH 13.

Analysis. Calcd. for C$_{12}$H$_{14}$N$_2$O$_4$·0.1H$_2$O: C, 57.18; H, 5.68; N, 11.12. Found: C, 56.91; H, 5.86; N, 10.82.

EXAMPLE 5

5-Ethyl-1-[(1α,3β,4α)-3-Hydroxy-4-(hydroxymethyl)-cyclopentyl]-2,4(1H,3H)-pyrimidinedione (The Carbocyclic Analogue of 5-Ethyl-2'-deoxyuridine, C-EDU, Formula 8, R=H) From the 5-Ethynyl Derivative of Example 4

Procedure A. A mixture of the 5-ethynylpyrimidine (50 mg) of Example 4, a hydrogenation catalyst (60 mg of commercial 5% palladium-on-calcium carbonate containing lead), quinoline (0.2 mL), and acetone (10 mL) was treated with hydrogen at approximately atmospheric pressure. After 20 min. of stirring in the hydrogen atmosphere, the mixture was filtered to remove the catalyst, and the filtrate (including ethanol washings of the catalyst) was concentrated to dryness in vacuo. The crude product was purified by chromatography on a column of silica gel 60 (15 g) with 9:1 chloroform-methanol as the developing and eluting solvent. Effluent fractions that were shown by means of a recording UV monitor to contain the desired product were combined and concentrated to dryness. The residue was triturated with ethyl acetate (2 mL), and the white crystalline product (C-EDU) was collected by filtration, washed with ethyl acetate, and dried in vacuo at 56° C.: yield, 63% (32 mg); mp 148°–151° C. (capillary inserted at 45° C., heating rate 3° C./min.); TLC, 1 spot (5:1 chloroform-methanol); UV max 274 nm ($\epsilon$ 10300) at pH 1, 273 ($\epsilon$ 10500) at pH 7, and 271 ($\epsilon$ 8000) at pH 13; MS (electron-impact, direct-probe temperature 200° C.), m/e 254 (M), 239 (M—CH$_3$), 224 (M—CH$_2$OH+H), 195 (M—CO—CH$_2$OH), 167 (P+C$_2$H$_4$), 141 (P+2H), 140 (P+H); IR (1800–1300 cm$^{-1}$ region) 1685 vs, 1670 vs, 1640, 1515 w, 1475, 1465, 1435 w, 1420, 1390, 1370, 1335, 1315; $^1$H-NMR (Me$_2$SO-d$_6$) $\delta$1.02 t (CH$_3$), 1.42 m and 2.05 m (CH$_2$, position 5 of the cyclopentyl group), 1.7–2.0 m (CH$_2$ position 2 of the cyclopentyl group), 1.91 m (CH, position 4 of the cyclopentyl group), 2.22 q (CH$_2$ of the ethyl group), 3.45 m (CH$_2$ of CH$_2$OH), 3.98 m (CHOH, position 3 of the cyclopentyl group), 4.60 t (HO of CH$_2$OH), 4.70 d (HO at position 3 of the cyclopentyl group), 4.96 m (CH, position 1 of the cyclopentyl group), 7.47 s (CH, position 6 of the pyrimidine ring), 11.16 s (NH of pyrimidine ring).

Analysis. Calcd. for $C_{12}H_{18}N_2O_4$: C, 56.68; H, 7.14; N, 11.02. Found: C, 56.30; H, 7.16; N, 10.97.

Procedure B. A suspension of the 5-ethynylpyrimidine (100 mg) of Example 4 and 5% palladium-on-charcoal catalyst in ethanol (10 mL) was treated with hydrogen at approximately atmospheric pressure. After 1 hr. in the hydrogen atmosphere, the mixture was filtered to remove the catalyst, and the filtrate (including ethanol washings of the catalyst) was concentrated to a residue that crystalized when it was triturated with ether. The white crystals were collected by filtration, washed with ether, and dried in vacuo at 56° C.: yield, 90% (92 mg.). The IR and $^1$H-NMR spectra of this material showed that it was crude C-EDU.

EXAMPLE 6

1-[(1α,3β,4α)-3-Hydroxy-4-(hydroxymethyl)cyclopentyl]-5-[2-(trimethylsilyl)ethyl]-2,4(1H,3H)-pyrimidinedione Diacetate (Formula 7, R=Acetyl)

A mixture of the 5-(trimethylsilylethynyl)pyrimidine (173 mg) of Example 3, ethanol (20 mL), and 5% palladium-on-charcoal (100 mg) was stirred for 45 min. in an atmosphere of hydrogen at approximately atmospheric pressure. The mixture was filtered to remove the catalyst, and the filtrate (including ethanol washings of the catalyst) was concentrated in vacuo to a colorless syrup: yield, 173 mg (99%). The mass spectrum (FAB) of this material showed that it was the compound represented by Formula 7 with R=CH$_3$CO: m/e 411 (M+1), 395 (M−CH$_3$), 351 (395−CH$_3$CO−H), 213 (P+2H), 197.

EXAMPLE 7

1-[(1α,3β,4α)-3-Hydroxy-4-(hydroxymethyl)cyclopentyl]-5-[2-(trimethylsilyl)ethyl]-2,4(1H,3H)-pyrimidinedione (Formula 7, R=H)

A solution of the diacetate (170 mg) of Example 6 in ammonia-methanol (17 mL, 10% ammonia) was stirred at room temperature overnight. The reaction solution was concentrated under reduced pressure to a syrupy residue. The desired product (Formula 7 with R=H) was isolated by chromatography on silica gel with 5:1 chloroform-methanol as the developing and eluting solvent. The collection of fractions was monitored by TLC; fractions containing the desired product were combined and concentrated under reduced pressure. Further concentration in vacuo with a vacuum pump left a crystalline residue that was triturated with 1:1 ethyl acetate-cyclohexane (3 mL). The crystalline product was collected by filtration, washed with the same solvent, and dried in vacuo at 78° C.: yield, 68 mg (50%); mp 154°–156° C. (inserted at 100° C., 3° C./min.); TLC, 1 spot (5:1 chloroform-methanol); MS (FAB), m/e 327 (M+1), 311 (M−CH$_3$), 213 (P+2H), 197.

Analysis. Calcd. for $C_{15}H_{26}N_2O_4Si$: C, 55.18; H, 8.03; N, 8.58. Found: C, 55.16; H, 8.01; N, 8.46.

EXAMPLE 8

Tribenzoyl Derivative of the Carbocyclic Analogue of Thymidine (Formula 10 with X=H and R′=Phenyl)

A solution consisting of 5.0 mL of benzoyl chloride, 2.0 g of the carbocyclic analogue (Formula 9) of thymidine; and 100 mL of dry pyridine was heated at 57°–58° C. for 70 hr. The reaction solution was added slowly to a water-ice mixture (800 mL), and the amorphous precipitate that formed was extracted into chloroform (total, 300 mL). The chloroform solution was washed successively with three 100-mL portions of 0.1N hydrochloric acid, saturated sodium bicarbonate solution, and water. The organic layer was dried with magnesium sulfate, filtered, and concentrated in vacuo to a yellow gum (weight 4.3 g). This material was purified by chromatography on a column of silica gel 60 (150 g) with 9:1 chloroform-methanol as the developing and eluting solution. The fractions that contained the tribenzoyl derivative (Formula 10 with X=H and R′=phenyl) were selected by TLC and were combined and concentrated in vacuo to a white glass; yield, 4.02 g (88%). This material was soluble in ethanol and in ethyl acetate, but not in ether. When cyclohexane was added to an ethyl acetate solution of the glassy product, an amorphous precipitate formed. The solvents were evaporated under reduced pressure, and the white glass was kept in vacuo at 56° C. for 3 hr. and then submitted for analysis: MS (electron impact, direct-probe temperature 250° C.), m/e 552 (M), 524, 482, 447 (M−$C_6H_5CO$), 430 (M−$C_6H_5COOH$), 326, 325, 203, 126, 122 ($C_6H_5COOH$), 105 ($C_6H_5CO$); $^1$H-NMR (CDCl$_3$) δ1.77 m and 2.52 m (CH$_2$, position 5 of the cyclopentyl group), 1.91 s (CH$_3$), 2.37 m (CH$_2$, position 2 of the cyclopentyl group), 2.75 m (CH, position 4 of the cyclopentyl group), 4.52 d (CH$_2$ of —CH$_2$OCOC$_6$H$_5$), 5.22 qn (CH, position 1 of the cyclopentyl group), 5.46 m (CH, position 3 of the cyclopentyl group), 7.15 s (CH, position 6 of the pyrimidinyl group), 7.32–7.67 m (CH, positions 3, 4, and 5 of the phenyl groups), 7.86–8.06 m (CH, positions 2 and 6 of the phenyl groups).

Analysis. Calcd. for $C_{32}H_{28}N_2O_7 \cdot 0.5$ ethyl acetate: C, 68.44; H, 5.41; N, 4.69. Found: C, 68.62; H, 5.18; N, 4.41.

EXAMPLE 9

Tribenzoyl Derivative of 5-(Bromomethyl)-1-[(1α,3β,4α)-3-hydroxy-4-(hydroxymethyl)cyclopentyl]-2,4(1H,3H)-pyrimidinedione (Formula 10 with X=Br and R′=Phenyl).

A mixture of the tribenzoyl derivative (1.26 g) of Example 8, N-bromosuccinimide (504 mg), and carbon tetrachloride (120 mL) was boiled under reflux for 1 hr. and simultaneously was exposed to light from a 150-Watt flood lamp that was 10 cm from the reaction flask. The hot solution was decanted from a tarry precipitate and was concentrated in vacuo and under anhydrous conditions to a glassy residue: weight, 1.43 g. The mass spectrum and the proton NMR spectrum showed that the product was predominantly the compound represented by Formula 10 with X=Br and R′=phenyl: MS (electron-impact, direct-probe temperature 250° C.), m/e 630 (M), 551 (M−Br), 323 (M−P); $^1$H-NMR (CDCl$_3$) δ1.83 m and 2.57 m (CH$_2$, position 5 of the cyclopentyl group), 2.43 m (CH$_2$, position 2 of the cyclopentyl group), 2.78 m (CH, position 4 of the cyclopentyl group), 4.24 s (CH$_2$Br), 4.56 d (CH$_2$OCOPh), 5.22 m (CH, position 1 of the cyclopentyl group), 5.49 m (CH, position 3 of the cyclopentyl group), 7.59 s (CH, position 6 of the pyrimidinyl group), 7.42 m and 7.51 m (positions 3 and 5 of the phenyl groups), 7.57 m and 7.66 m (position 4 of the phenyl groups), 7.92 m and 8.01 m (positions 2 and 6 of the phenyl groups).

EXAMPLE 10

1-[(1α,3β,4α)-3-Hydroxy-4-(hydroxymethyl)cyclopentyl]-5-methyl-2,4(1H,3H)-pyrimidinedione Dibenzoate (Dibenzoyl Derivative of the Carbocyclic Analogue of Thymidine, Formula 11 with X=H and R'=Phenyl)

A solution consisting of 1.15 g of the tribenzoyl derivative of Example 8, 133 mL of ethanol, 60 mL of water, and 7.2 mL of 1N hydrochloric acid was heated under gentle reflux for 24 hrs. The reaction solution was concentrated to remove ethanol, and the aqueous mixture (containing a colorless syrup) was extracted twice with 50-mL portions of chloroform. The total chloroform extract was washed with saturated aqueous sodium bicarbonate solution, dried with magnesium sulfate, filtered, and concentrated under reduced pressure to a colorless gum. The residue was mixed well with ethanol (15 mL); the mixture (containing white crystals) was stored in a freezer ($-20°$ C.); and the crystalline product was collected by filtration, washed with cold ethanol, and dried in vacuo: yield, 725 mg (78%); mp 173°–176° C.; mass spectrum (FAB), m/e 449 (M+1), 327 (M−$C_6H_5COO$); $^1$H-NMR ($CDCl_3$) δ1.73 m and 2.50 m ($CH_2$, position 5 of the cyclopentyl group), 1.89 s ($CH_3$), 2.35 m ($CH_2$, position 2 of the cyclopentyl group), 2.77 m ($CH$, position 4 of the cyclopentyl group), 4.54 d ($CH_2OCOPh$), 5.24 qn ($CH$, position 1 of the cyclopentyl group), 5.47 m ($CH$, position 3 of the cyclopentyl group), 7.06 s ($CH$, position 6 of the pyrimidinyl group), 7.42 m ($CH$, positions 3 and 5 of the phenyl groups), 7.56 m ($CH$, position 4 of the phenyl groups), 8.01 m ($CH$, positions 2 and 6 of the phenyl groups).

Analysis. Calcd. for $C_{25}H_{24}N_2O_6$: C, 66.95; H, 5.39; N, 6.25. Found: C, 66.67; H, 5.77; N, 6.41.

EXAMPLE 11

5-(Bromomethyl)-1-[(1α,3β,4α)-3-Hydroxy-4-(hydroxymethyl)cyclopentyl]-2,4(1H,3H)-pyrimidinedione Dibenzoate (Formula 11 with X=Br and R'=$C_6H_5$)

A mixture of N-bromosuccinimide (149 mg), 300 mg of the carbocyclic analogue (Formula 11 with X=H and R'=phenyl) of thymidine dibenzoate, and dry carbon tetrachloride (34 mL) was boiled under reflux for 1 hr. and simultaneously was exposed to light (provided by a 150-Watt flood lamp). The colorless solution was decanted from a waxy precipitate and was concentrated in vacuo under anhydrous conditions to a gummy residue; yield, 99% (350 mg). The mass spectrum and the $^1$H-NMR spectrum of this material demonstrated that it was predominantly the desired 5-(bromomethyl)uracil derivative (Formula 11 with X=Br and R'=phenyl): MS (FAB), m/e 447 (M−Br), 405 (M−$C_6H_5COO$), 323 (M−P); $^1$H-NMR ($CDCl_3$) δ1.82 m and 2.55 m ($CH_2$, position 5 of the cyclopentyl group), 2.41 s ($CH_2$, position 2 of the cyclopentyl group), 2.8 m ($CH$, position 4 of the cyclopentyl group), 4.23 d ($CH_2Br$), 4.57 d ($CH_2OCOPh$), 5.21 qn ($CH$, position 1 of the cyclopentyl group), 5.52 m ($CH$, position 3 of the cyclopentyl group), 7.49 s ($CH$, position 6 of the pyrimidinyl group), 7.45 m ($CH$, positions 3 and 5 of the phenyl groups), 7.58 m (position 4 of the phenyl groups), 8.04 m (positions 2 and 6 of the phenyl groups).

EXAMPLE 12

5-Ethyl-1-[(1α,3β,4α)-3-Hydroxy-4-(hydroxymethyl)cyclopentyl]-2,4(1H,3H)-pyrimidinedione Dibenzoate (C-EDU Dibenzoate, Formula 12 with R''=Methyl and R'=Phenyl)

A solution of the 5-bromomethyl)uracil derivative (350 mg) of Example 11 in a mixture of dry ether (10 mL) and dry tetrahydrofuran (5 mL) was prepared under an argon atmosphere and was cooled to $-15°$ C. A solution of the lithium dimethylcopper reagent was then prepared as follows. A suspension of cuprous iodide (1.43 g) in dry ether (25 mL) was prepared under an argon atmosphere and was cooled to $-15°$ C. To this stirred suspension was added dropwise (during approximately 10 min.) a 1.5M solution (10 mL) of methyllithium in ether. A yellow precipitate formed initially, but the reaction mixture later became clear. A portion (5.6 mL) of the solution of lithium dimethylcopper was added dropwise to the stirred, cold ($-15°$ C.) solution of the 5-(bromomethyl)uracil derivative, and the resulting mixture was kept at 3° C. overnight. An aqueous solution of ammonium chloride (5%, 15 mL) was added to the reaction mixture, and the resulting mixture was stirred at room temperature for 1 hr. and then extracted twice with chloroform (2×30 mL). The total chloroform extract was washed with water, dried over magnesium sulfate, filtered, and concentrated under reduced pressure to a syrup. The desired product (C-EDU dibenzoate) was isolated by chromatography on silica gel 60 with 1:1 ethyl acetate-benzene as the developing and eluting solvent. The collection of fractions was monitored by TLC; fractions containing C-EDU dibenzoate were combined and concentrated in vacuo to a white solid foam: yield, 40% (120 mg.); mass spectrum (FAB), m/e 463 (M+1), 341 (M−$C_6H_5COO$).

EXAMPLE 13

5-Ethyl-1-[1α,3β,4α-3-hydroxy-(4-hydroxymethyl)cyclopentyl]-2,4(1H,3H)-pyrimidinedione (C-EDU, Formula 8 with R=H or Formula 13 with R''=$CH_3$) From the Dibenzoyl Derivative of Example 12

A solution of 115 mg of the dibenzoyl derivative of C-EDU in an ammonia-methanol solution (10 mL, 10% ammonia) was stirred at room temperature for 2.5–3 days. The reaction solution was concentrated under reduced pressure to a syrupy residue. C-EDU was isolated by applying a methanol solution of the residue to a preparative TLC plate of silica gel and developing the chromatogram with 5:1 chloroform-methanol. The principal band was scraped from the plate and extracted in a Soxhlet extractor with hot ethanol for 2 hr. The ethanol extract was concentrated to dryness, a small amount of ethanol was added, the mixture was filtered, and the filtrate was concentrated under reduced pressure to a colorless syrup. The residue was triturated with ethyl acetate, and the resulting white crystalline solid was collected by filtration, and dried in vacuo: yield, 41 mg (65%); mp 147°–150° C. (capillary inserted at 50° C., heating rate 3° C./min.); TLC, 1 spot (5:1 chloroform-methanol); MS (FAB), m/e 255 (M+1), 141 (P+2H). The melting point of a mixture of this material and the specimen described in Procedure A of Example 5 was 147°–150° C. (capillary inserted at 50° C., 3° C./min.). When this material and the specimen of C-EDU described in Example 5 were applied side-by-side on a TLC plate of silica gel, they moved side-byside ($R_f$ ca. 0.5) when the chromatogram was developed with 5:1 chloroform-methanol. Similarly, reverse-phase HPLC ($\mu$ Bondapak C18 column; solvent 90:10 0.01M aqueous ammonium dihydrogen phosphate-methanol, isocratic) of the two specimens monitored at 254 nm showed that their retention times (15.46 min. and 15.45 min.) were the same. The IR spectrum of the specimen obtained by the method described in this Example was identical with the IR spectrum of the specimen of C-EDU described in Example 5. Thus, the melting temperatures, TLC, HPLC, and the IR spectra show that the specimens of Example 5 and 13 are identical.

EXAMPLE 14

Antiviral Activity of Carbocyclic Analogues of Some Thymine Nucleosides

Carbocyclic analogues of thymine nucleosides were tested for antiviral activity against viruses that replicate in mammalian cells growing in cell culture. The results of these tests against herpes simplex viruses are summarized in Table 1. The Virus rating (VR) is a weighted measurement of antiviral activity determined by the method of Ehrlich et al., *Annals of the New York Academy of Science*, volume 130, pages 5–16, 1965. In tests carried out by this method, a VR of 0.5–0.9 indicates marginal to moderate antiviral activity, and a VR equal to or greater than 1 indicates definite antiviral activity. The higher the value of VR, the greater is the antiviral activity. The $MIC_{50}$ (minimum inhibitory concentration, 50%) is the concentration of a test compound required for 50% inhibition of virus-induced cytopathogenic effects.

The results summarized in Table 1 demonstrate that the carbocyclic analogue (C-EDU, Formula 8 with R=H) of 5-ethyl-2'-deoxyuridine inhibits the replication of both type 1 herpes simplex virus (HSV-1) and type 2 herpes simplex virus (HSV-2). The results summarized in Table 1 also show that the carbocyclic analogue of 5-ethynyl-2'-deoxyuridine has significant, selective activity against both HSV-1 and HSV-2 and that the carbocyclic analogue of 5-trimethylsilylethyl-2'-deoxyuridine has activity against HSV-1.

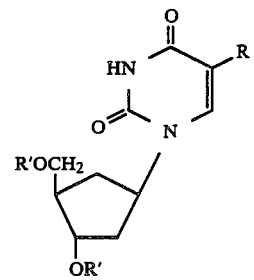

wherein

R is a group having the formula $-C\equiv CSi(CH_3)_3$, $-C\equiv CH$, $-CH=CH_2$, $-CH_2CH_2Si(CH_3)_3$ or $-CH_2X$; X is bromo, chloro or iodo; and R' is hydrogen, an acetyl group or a benzoyl group, with the proviso that when R is $-CH_2X$, R' is an acetyl group or a benzoyl group.

2. A compound as defined in claim 1 wherein R is $-C\equiv CSi(CH_3)_3$.

3. A compound as defined in claim 2 wherein R' is acetyl.

4. A compound as defined in claim 1 wherein R is $-C\equiv CH$.

5. A compound as defined in claim 4 wherein R' is hydrogen.

6. A compound as defined in claim 1 wherein R is $-CH_2CH_2Si(CH_3)_3$.

7. A compound as defined in claim 6 wherein R' is acetyl.

8. A compound as defined in claim 6 wherein R' is hydrogen.

9. A compound as defined in claim 1 wherein R is $-CH_2X$ and X is bromo, chloro or iodo.

10. A compound as defined in claim 9 wherein X is Br and R' is benzoyl.

11. A process for the treatment of a host animal having a herpes virus infection which comprises administering to said host animal a therapeutically effective amount of a compound as defined in claim 5.

12. A process for the treatment of a host animal hav-

TABLE 1

| | Antiviral Activity of Carbocyclic Analogues of Thymine Nucleosides | | | | |
|---|---|---|---|---|---|
| | | Herpes Simplex Virus | | | |
| | | Type 1, Strain 377 | | Type 2, Strain MS | |
| Compound | Host[a] Cells | VR | $MIC_{50}$ mcg./ml. | VR | $MIC_{50}$ mcg./ml. |
| Carbocyclic analogue of 5-ethynyl-2'-deoxyuridine (Formula 6 with R = H, Example 4) | Vero | 0.9 | 253 | 1.1 | 207 |
| Carbocyclic analogue of 5-trimethylsilylethyl-2'-deoxyuridine (Formula 7 with R = H, Example 7) | Vero | 0.5 | 320 | | |
| C-EDU (Formula 8 with R = H, Examples 5 or 13) | Vero | 2.4 | 45 | 1.1 | 227 |
| | | 2.1 | 69 | 1.1 | 178 |
| EDU[b] | Vero | 2.3 | 19 | 2.2 | 321 |
| Ara-A[b] | Vero | 2.0–2.1 | 15–19 | 1.3–1.7 | 22–45 |

[a]Antiviral evaluations were performed with HSV-1 or HSV-2 replicating in Vero cells.
[b]9-β-D-Arabinofuranosyladenine (Ara-A) and the true nucleoside 5-ethyl-2'-deoxyuridine (EDU) were tested as positive controls.

We claim:

1. A compound having the formula ing a herpes virus infection which comprises administering to said host animal a therapeutically effective amount of a compound as defined in claim 8.

13. A compound having the formula
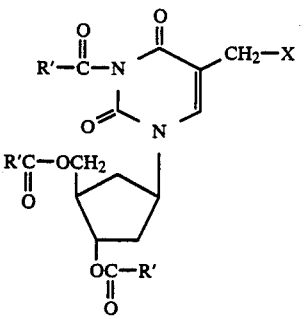
wherein X is hydrogen, bromo, chloro or iodo and R' is a phenyl group.
14. A compound as defined in claim 13 wherein X is hydrogen.
15. A compound as defined in claim 13 wherein X is bromo.
* * * * *